United States Patent
Abels et al.

(10) Patent No.: US 6,963,788 B2
(45) Date of Patent: Nov. 8, 2005

(54) HOLOGRAPHY-AIDED ORTHODONTIC ARCHWIRE BENDING

(76) Inventors: Norbert Abels, Alleestrasse 30a, 66424 Homburg (DE); Claus H. Backes, St. Wendeler Strasse 45, 66113 Saarbrücken (DE)

( * ) Notice: Subject to any disclaimer, the term of this patent is extended or adjusted under 35 U.S.C. 154(b) by 211 days.

(21) Appl. No.: 10/382,260

(22) Filed: Mar. 4, 2003

(65) Prior Publication Data

US 2004/0176866 A1 Sep. 9, 2004

(51) Int. Cl.⁷ .............................. G06F 19/00; A61C 3/00
(52) U.S. Cl. ......................... 700/117; 700/98; 700/185; 433/24; 433/29
(58) Field of Search ............................ 700/96–98, 117, 700/118, 184, 185; 433/20, 24, 29; 29/896.11

(56) References Cited

U.S. PATENT DOCUMENTS

| | | | |
|---|---|---|---|
| 4,131,472 A | 12/1978 | MacDonald, Jr. et al. | 96/38.3 |
| 4,764,012 A * | 8/1988 | Ryden et al. | 356/457 |
| 4,973,114 A | 11/1990 | Edwardson et al. | 350/3.83 |
| 5,011,405 A | 4/1991 | Lemchen | 433/24 |
| 5,295,886 A | 3/1994 | Wildman | 433/24 |
| 5,447,432 A * | 9/1995 | Andreiko et al. | 433/24 |
| 5,474,448 A | 12/1995 | Andreiko et al. | 433/24 |
| 5,533,895 A | 7/1996 | Andreiko et al. | 433/24 |
| 5,569,578 A * | 10/1996 | Mushabac | 433/215 |
| 5,674,337 A | 10/1997 | Coombs et al. | 156/71 |
| 6,210,162 B1 | 4/2001 | Chishti et al. | 433/213 |
| 6,217,325 B1 | 4/2001 | Chishti et al. | 433/24 |
| 6,250,918 B1 | 6/2001 | Sachdeva et al. | 433/24 |
| 6,309,215 B1 | 10/2001 | Phan et al. | 433/24 |
| 6,315,553 B1 | 11/2001 | Sachdeva et al. | 433/24 |
| 6,318,994 B1 | 11/2001 | Chishti et al. | 433/24 |
| 6,350,120 B1 * | 2/2002 | Sachdeva et al. | 433/24 |
| 6,413,084 B1 | 7/2002 | Rubbert et al. | 433/29 |
| 6,431,870 B1 | 8/2002 | Sachdeva | 433/213 |
| 6,464,496 B1 | 10/2002 | Sachdeva et al. | 433/24 |
| 6,540,512 B1 | 4/2003 | Sachdeva et al. | 433/24 |
| 6,632,089 B2 * | 10/2003 | Rubbert et al. | 433/24 |
| 6,776,614 B2 * | 8/2004 | Wiechmann et al. | 433/24 |
| 2002/0025503 A1 * | 2/2002 | Chapoulaud et al. | 433/24 |
| 2002/0156652 A1 | 10/2002 | Sachdeva et al. | 705/2 |
| 2003/0056561 A1 | 3/2003 | Butscher et al. | 72/295 |
| 2003/0195725 A1 * | 10/2003 | Hashash | 703/2 |

OTHER PUBLICATIONS

"A New Bracket System for Linqual Orthodontic Treatment"; Part 1: Theoretic Background and Development Journal of Orofacial Orthopedics; Dirk Wiechmann; JOrofac Orthop/Fortschr Kieferorthop 2002, No. 3 pp. 234–245.

* cited by examiner

*Primary Examiner*—Paul Rodriguez
(74) *Attorney, Agent, or Firm*—Workman Nydegger

(57) ABSTRACT

Mechanisms for facilitating and performing precision bending of an orthodontic bracket archwire. A digital representation of an ideal bent orthodontic bracket archwire is obtained. The digital representation is then used to generate a holographic image of the bent orthodontic bracket archwire. The orthodontist then has a three-dimensional image to use as a guide in properly bending an actual physical archwire.

12 Claims, 5 Drawing Sheets

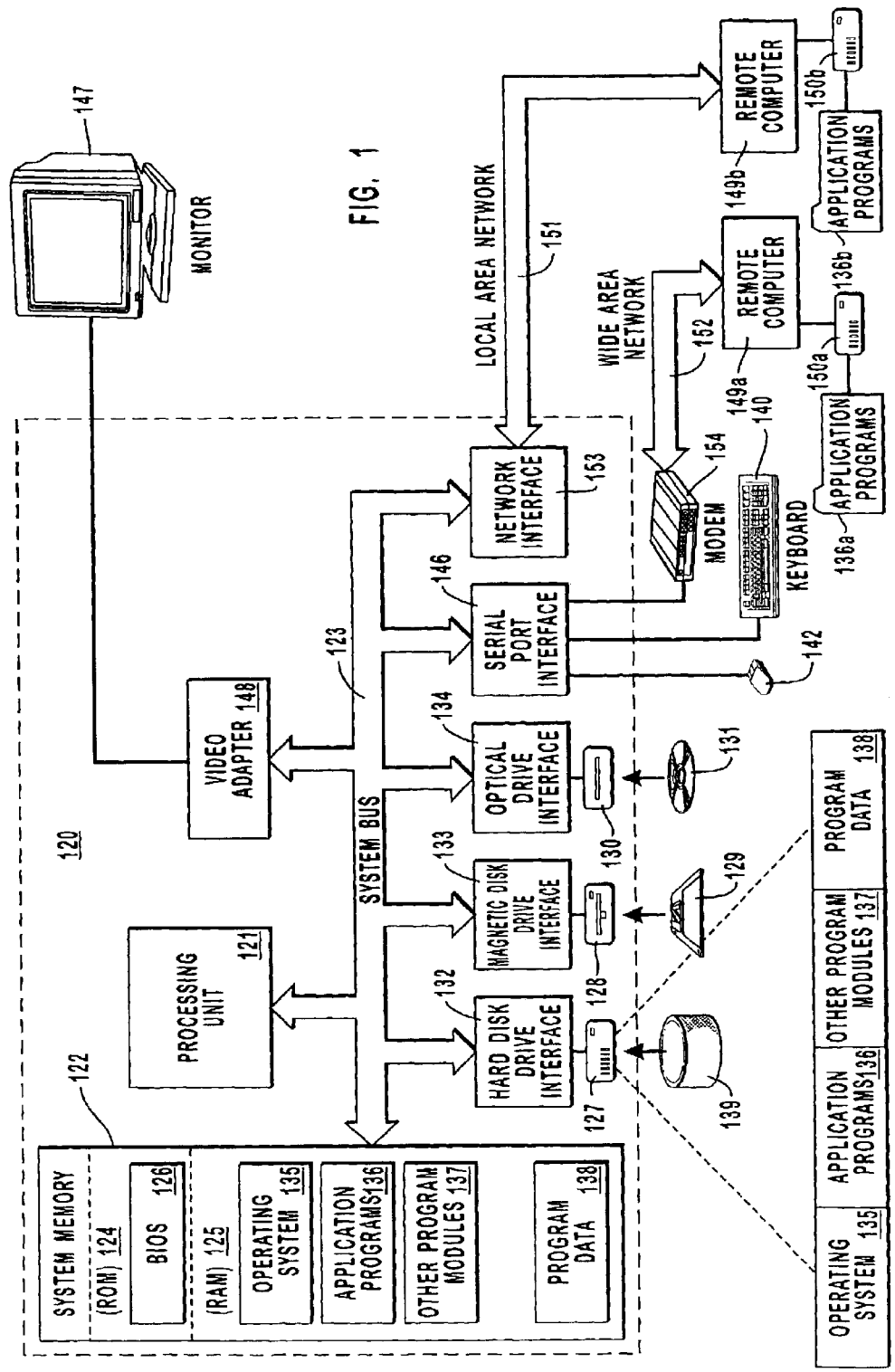

HOLOGRAPHY-AIDED ORTHODONTIC ARCHWIRE BENDING

BACKGROUND OF THE INVENTION

1. The Field of the Invention

The present invention relates to orthodontics, and more specifically, to technologies for using holography to assist in the precision bending of an orthodontic archwire.

2. Background and Related Art

An individual's jaw, gums and teeth (also referred to herein as an "orthodontic structure") combine to provide a critical function by allowing the individual to mechanically break down food for safer swallowing and more efficient digestion. Sever malformations or mechanical flaws of the individual's orthodontic structure may also interfere (even if only slightly) with the proper articulation of language. The abilities to properly eat and speak fluidly are essential needs of mankind. Any degradation in these abilities may have a significant impact on the affected individual's quality of living.

Also, human beings have varying concerns about their own appearance and how they are perceived by others. In addition, some human beings are sometimes inclined (even if on a subconscious level) to form negative judgments about an individual if the appearance of the individual's teeth varies significantly from an ideal societal norm. Accordingly, individuals with such variances may desire for better conformance of the teeth with societal norms, whether their motivation be for the proper functioning of the orthodontic structure, or whether their motivation be for a better appearance, or a combination thereof.

Orthodontics is a now highly-advanced branch of medicine in which dental practices are implemented to manipulate a patient's orthodontic structure for better function and appearance. In order to perform such manipulation, it is necessary to apply sustained and appropriately-directed forces to the teeth. To apply such forces to the teeth, an orthodontist typically affixes brackets to a patient's teeth using bonding material. The orthodontist then couples an arched wire (often called an "archwire") to the brackets using an archwire slot formed in each of the brackets. Some of the teeth may have the archwire anchored to the correspondence bracket, while other teeth may have brackets that allow for some sliding of the archwire.

In order to achieve movement of teeth towards a desired corrected position, it is not only necessary that sustained force be applied, but also that that force be properly directed to achieve the specific movement desired. This requires the considerable knowledge and expertise held by licensed orthodontists. The orthodontist will use that expertise to properly place the brackets, and to properly bend the archwire. Despite such expertise, however, while the teeth may generally move towards the corrected position, there may be some slight errors in the forces applied by the archwire that become apparent from the path of movement of the teeth. Of course, there may be some degree of error in how the archwire is bent, thereby contributing to some of the deviations from ideal movement of the teeth towards a corrected position.

Accordingly, what would be advantageous are mechanisms that provide for more precise wire bending to thereby provide more precise correction of tooth movement towards a corrected position.

BRIEF SUMMARY OF THE INVENTION

The foregoing problems with the prior state of the art are overcome by the principles of the present invention, which are directed towards mechanisms for facilitating and performing precision bending of an orthodontic bracket archwire. The orthodontic bracket archwire applies the precision forces necessary to move teeth towards a corrected position. The archwire applies these forces when the archwire is connected to orthodontic brackets that are affixed to the teeth for corrective movement.

A digital representation of a bent orthodontic bracket archwire is obtained that is bent in a manner that would facilitate such corrective movement of the teeth if properly placed. A computer may calculate an estimated ideal bent configuration of the archwire. In addition, user input may also contribute to the appearance of the digital representation of the archwire. For example, a user such as an orthodontist may make modifications, however small, to the estimated ideal bent configuration of the archwire.

The digital representation is then used to generate a holographic image of the bent orthodontic bracket archwire. The orthodontist then has a three-dimensional image to use as a guide in properly bending an actual physical archwire. For example, the orthodontist might try to bend the archwire so that it is congruent with the holographic image of the bent orthodontic bracket archwire. Accordingly, the archwire bending may be more precise than if the holographic image was not present as a guide. Furthermore, an expensive mechanical bending robot was not needed in order to obtain high precision in archwire bending.

Additional features and advantages of the invention will be set forth in the description that follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 illustrates a suitable computing environment in which the present invention may be employed;

DETAILED DESCRIPTION OF THE PREFERRED EMBODIMENTS

Figure 2A:
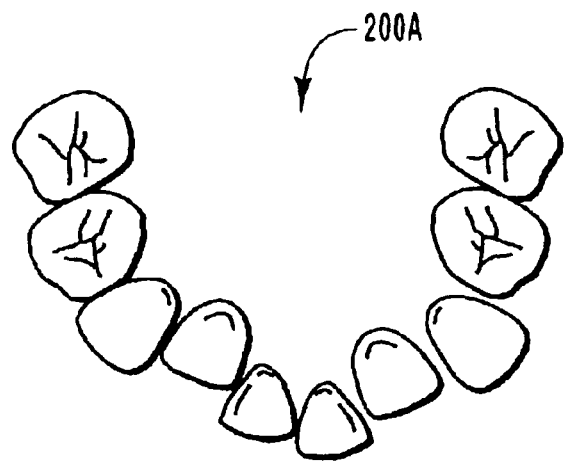
FIG. 2A illustrates a top view of uncorrected lower teeth.

The principles of the present invention involve mechanisms for facilitating and performing precision bending of an orthodontic bracket archwire. A digital representation of an ideal bent orthodontic bracket archwire is obtained. The digital representation is then used to generate a holographic image of the bent orthodontic bracket archwire. The orthodontist then has a three-dimensional image to use as a guide in properly bending an actual physical archwire.

Embodiments within the scope of the present invention include computer-readable media for carrying or having computer-executable instructions or data structures stored thereon. Such computer-readable media can be any available media which can be accessed by a general purpose or special purpose computer. By way of example, and not limitation, such computer-readable media can comprise physical computer-readable media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer.

When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, any instructions and data which cause a general purpose computer, special purpose computer, or special purpose processing device to perform a certain function or group of functions. The computer-executable instruction may be, for example, binaries, intermediate format instructions such as assembly language, or even source code. In accordance with the present invention, such computer-executable instructions may be used to assist users in the practice of orthodontics by causing a three-dimensional holographic image of a bent orthodontic archwire for the user to refer to when manually bending the real archwire.

FIG. 1 and the following discussion are intended to provide a brief, general description of a suitable computing environment in which the invention may be implemented. The example computing environment described herein is just one of an innumerable variety of computing systems that have processing and memory capability, and that may be configured to implement the principles of the present invention.

Although not required, the invention will be described in the general context of computer-executable instructions, such as program modules, being executed by computers in network environments. Generally, program modules include routines, programs, objects, components, data structures, etc. that perform particular tasks or implement particular abstract data types.

With reference to FIG. 1, an exemplary system for implementing the invention includes a general purpose computing device in the form of a conventional computer 120, including a processing unit 121, a system memory 122, and a system bus 123 that couples various system components including the system memory 122 to the processing unit 121. The system bus 123 may be any of several types of bus structures including a memory bus or memory controller, a peripheral bus, and a local bus using any of a variety of bus architectures. The system memory includes read only memory (ROM) 124 and random access memory (RAM) 125. A basic input/output system (BIOS) 126, containing the basic routines that help transfer information between elements within the computer 120, such as during start-up, may be stored in ROM 124.

The computer 120 may also include a magnetic hard disk drive 127 for reading from and writing to a magnetic hard disk 139, a magnetic disk drive 128 for reading from or writing to a removable magnetic disk 129, and an optical disk drive 130 for reading from or writing to removable optical disk 131 such as a CD-ROM or other optical media. The magnetic hard disk drive 127, magnetic disk drive 128, and optical disk drive 130 are connected to the system bus 123 by a hard disk drive interface 132, a magnetic disk drive-interface 133, and an optical drive interface 134, respectively. The drives and their associated computer-readable media provide nonvolatile storage of computer-executable instructions, data structures, program modules and other data for the computer 120. Although the exemplary environment described herein employs a magnetic hard disk 139, a removable magnetic disk 129 and a removable optical disk 131, other types of computer readable media for storing data can be used, including magnetic cassettes, flash memory cards, digital video disks, Bernoulli cartridges, RAMs, ROMs, and the like.

Program code means comprising one or more program modules may be stored on the hard disk 139, magnetic disk 129, optical disk 131, ROM 124 or RAM 125, including an operating system 135, one or more application programs 136, other program modules 137, and program data 138. A user may enter commands and information into the computer 120 through keyboard 140, pointing device 142, or other input devices (not shown), such as a microphone, joy stick, game pad, satellite dish, scanner, or the like. These and other input devices are often connected to the processing unit 121 through a serial port interface 146 coupled to system bus 123. Alternatively, the input devices may be connected by other interfaces, such as a parallel port, a game port or a universal serial bus (USB). A monitor 147 or another display device is also connected to system bus 123 via an interface, such as video adapter 148. In addition to the monitor, personal computers typically include other peripheral output devices (not shown), such as speakers and printers.

The computer 120 may operate in a networked environment using logical connections to one or more remote computers, such as remote computers 149a and 149b. Remote computers 149a and 149b may each be another personal computer, a server, a router, a network PC, a peer device or other common network node, and typically include many or all of the elements described above relative to the computer 120, although only memory storage devices 150a and 150b and their associated application programs 136a and 136b have been illustrated in FIG. 1. The logical connections depicted in FIG. 1 include a local area network (LAN) 151 and a wide area network (WAN) 152 that are presented here by way of example and not limitation. Such networking environments are commonplace in office-wide or enterprise-wide computer networks, intranets and the Internet.

When used in a LAN networking environment, the computer 120 is connected to the local network 151 through a network interface or adapter 153. When used in a WAN networking environment, the computer 120 may include a modem 154, a wireless link, or other means for establishing communications over the wide area network 152, such as the Internet. The modem 154, which may be internal or external, is connected to the system bus 123 via the serial port interface 146. In a networked environment, program modules depicted relative to the computer 120, or portions thereof, may be stored in the remote memory storage device. It will be appreciated that the network connections shown are exemplary and other means of establishing communications over wide area network 152 may be used.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Figure 2B:
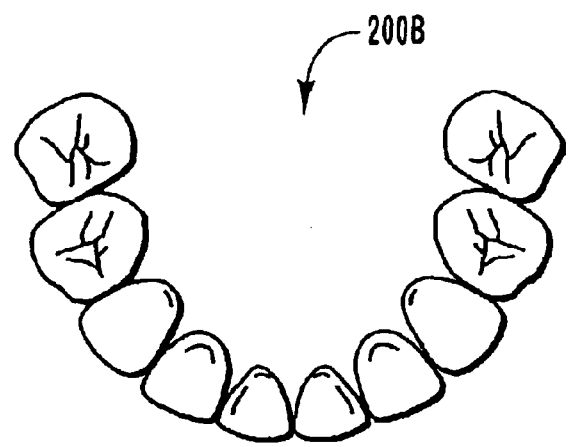
FIG. 2B illustrates a top view of the lower teeth after having been subject to orthodontic correction.

Orthodontics is a branch of dentistry that involves the correction or misaligned or incorrectly positioned teeth. FIG. 2A illustrates a top view of uncorrected lower teeth 200A, while FIG. 2B illustrates a top view of corrected lower teeth 200B. Note that a number of teeth in the uncorrected lower teeth 200A are misaligned or mispositioned as compared to their ideal position shown in FIG. 2B. In addition to the horizontal movement apparent from the top view, there may also be movement vertically in order to align the teeth along an occlusal plane. The occlusal plane is the imaginary surface on which upper and lower teeth meet.

Corrections such as those illustrated in FIG. 2B as compared to FIG. 2A, may be accomplished by applying precise forces to the teeth over extended periods of time. The teeth respond to such forces by gradually moving and rotating in the direction urged by the applied forces. One conventional method for applying such forces over a sustained period of time is to affix rigid brackets to each of the teeth. An archwire that is formed of resilient material may be bent and inserted into an archwire slot formed within each bracket. The archwire may be anchored to the brackets of some of the teeth (e.g., the most posterior molars), while being permitted to slide within the archwire slots of the remaining teeth.

The archwire has tendencies to return to its original undeformed position. Accordingly, the archwire will urge the teeth towards a position that results in the archwire attaining the archwire's original position. Accordingly, the forces that are applied to the teeth are heavily dependent on how the archwire is bent. In many cases, the teeth can attain very close to an ideal orientation and alignment with proper bending of the archwire. Any variation in the bending from ideal will result in slight errors in tooth movement towards a corrected position.

Figure 3:
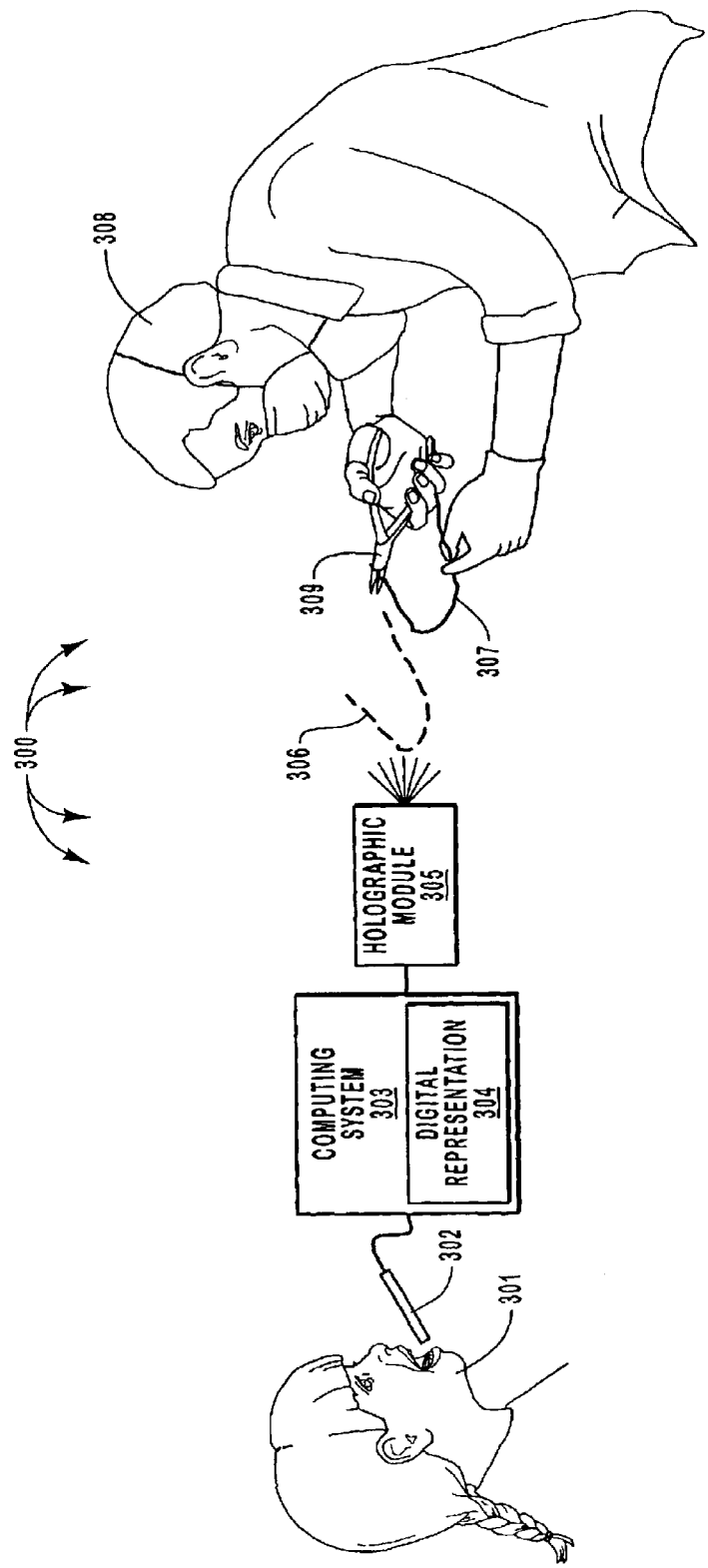
FIG. 3 illustrates a systematic view of a system for facilitating holography-aided orthodontic archwire bending in accordance with the principles of the present invention.

FIG. 3 illustrates a system 300 that uses a holographic image of an archwire to assist a user in manually bending a physical archwire. A computing system 303 acquires a digital representation 304 of an orthodontic structure 301 using, for example, a scanner 302. A holographic module 305 generates a holographic image 306 of a bent configuration of an orthodontic archwire. A user 308 such as an orthodontist may then use the holographic image to manually bend a physical archwire 307 using, for example, pliers 309. The computing system 303 may be structured as described above although there are any number of computing systems that may be configured as described herein to implement the features of the present invention.

Figure 4:
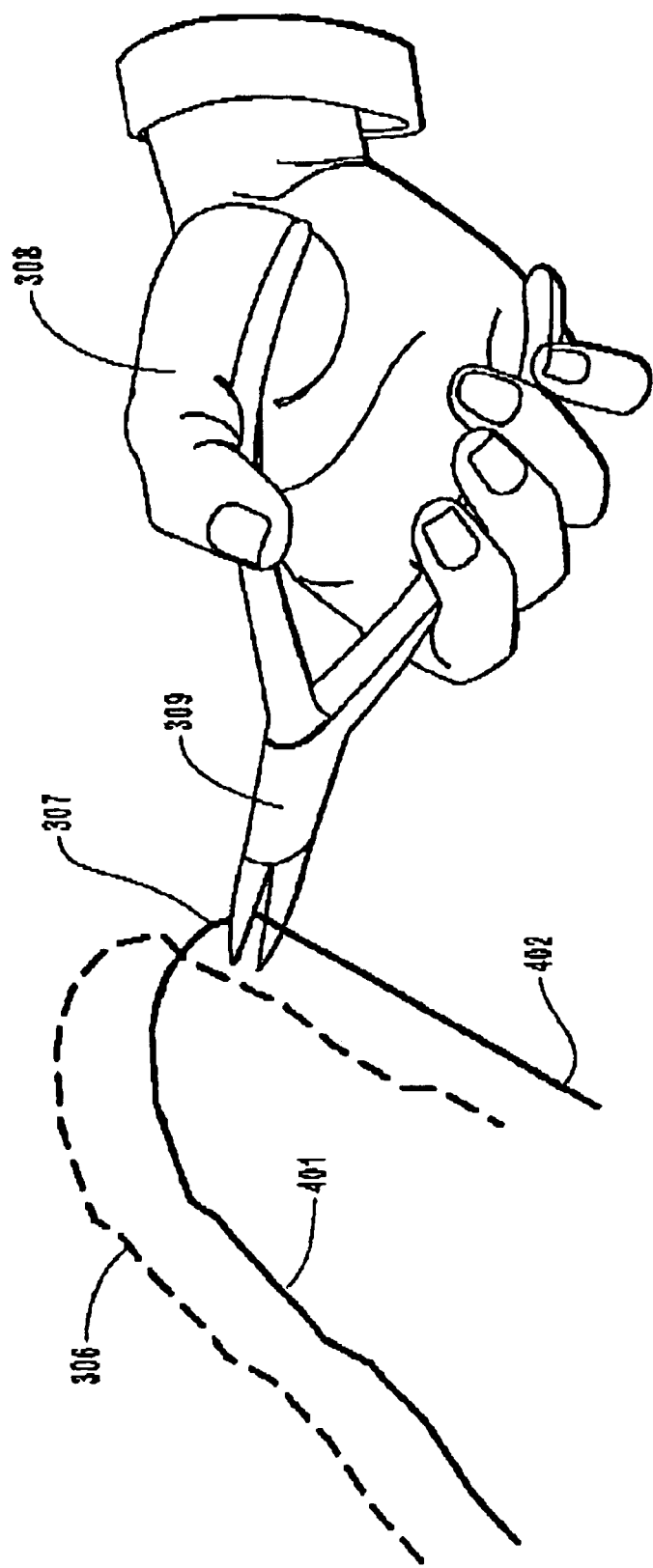
FIG. 4 illustrates the bending of a physical orthodontic bracket archwire using a holographic image of a suitably bend archwire.

FIG. 4 illustrates the holographic image 306 of the archwire being used as a guide for the bending of a physical archwire 307 in further detail. Note that portion 401 on the one side of pliers 309 is bent to closely match the form of the holographic image, while portion 402 is not yet bent. On one end of the spectrum, the holographic image may be a complete and continuous representation of the archwire. On the other end of the spectrum, the holographic image may just represent sample points at the points at which the archwire is to be bent. The holographic image may take any other form in between these two extremes so long as there are enough three-dimensional visual cues to give the orthodontist a mental image of how the archwire is to be bent.

Figure 5:
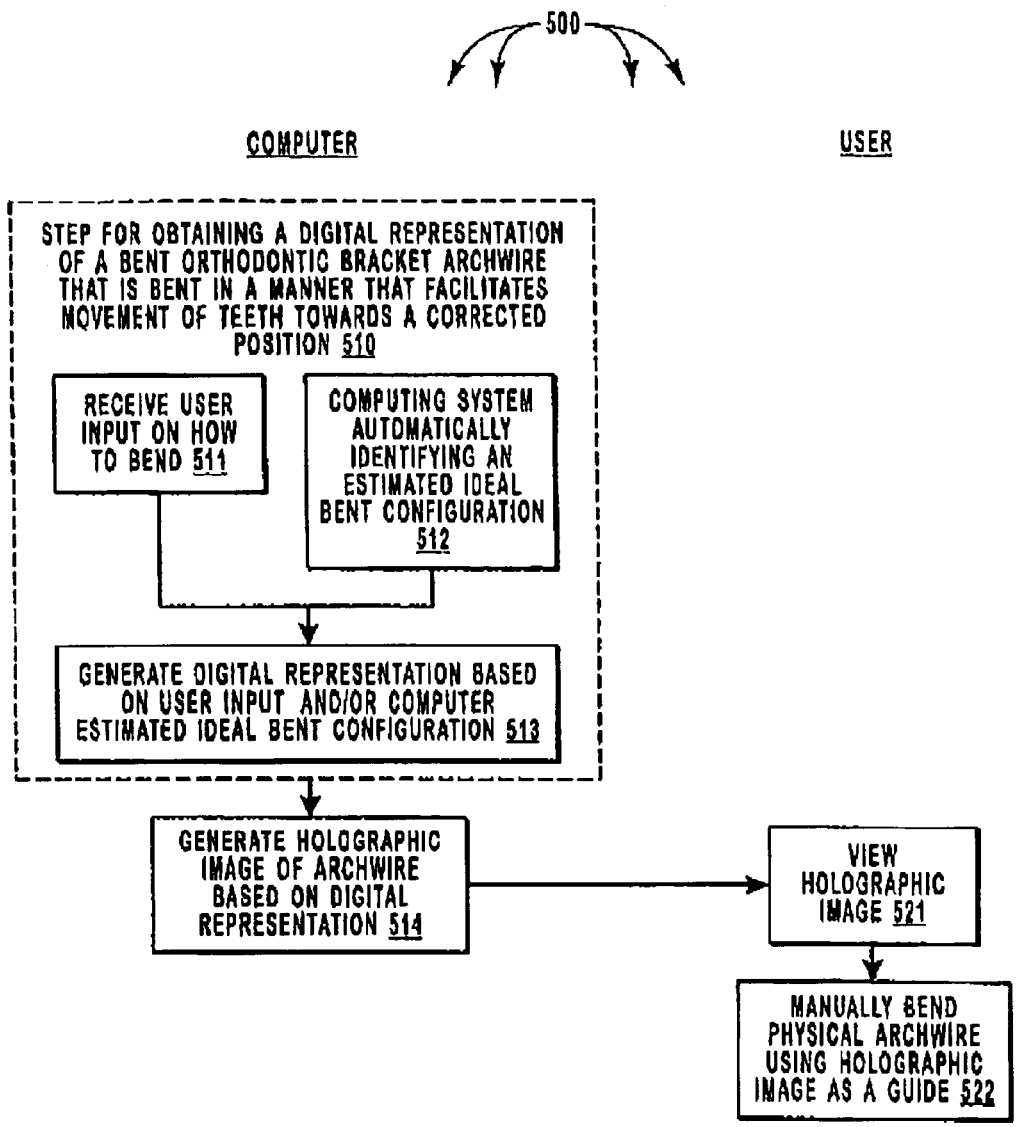
FIG. 5 illustrates a flowchart of a method for facilitating and performing holography-aided orthodontic archwire bending in accordance with the principles of the present invention.

FIG. 5 illustrates a flowchart of a method 500 for facilitating precision bending of an orthodontic bracket archwire that is to be connected to orthodontic brackets that either are affixed or will be affixed to the teeth of a patient. The Method 500 includes a step and several acts that are performed by the computing system 303 as represented in the left column of FIG. 5 under the heading "COMPUTER". Other acts are performed by the user as listed in the right column of FIG. 5 under the heading "USER".

Initially, method 500 includes a functional, result-oriented step for obtaining a digital representation of a bent orthodontic bracket archwire that is bent in a manner that facilitates movement of the teeth towards a corrected position when connected to the orthodontic brackets (step 510). This step may include any corresponding acts for accomplishing the stated result.

For example, the step 510 may include a corresponding act of receiving user input regarding how to bend an orthodontic bracket archwire (act 511). In the alternative, or in addition, the step 510 may include a corresponding act of the computing system automatically identifying an estimated ideal bent configuration of the orthodontic bracket archwire (act 512). The step 510 then may include a corresponding act of generating a digital representation of the bent orthodontic bracket archwire based at least in part on the received user input and/or the estimated ideal bent configuration (act 513). Accordingly, the digital representation may be established using user input, computed results, or a combination thereof.

In order to form the estimated ideal bent configuration of an archwire, the computer may first receive scanned data that represents the teeth that are to be corrected. The scanned data may be, for example, a three-dimensional digital representation of the teeth. A corrected form of the teeth may then be estimated by rotating and translating each tooth to a corrected position. This may be performed by a computer and/or by a user thereof where each tooth is represented as a separate moveable computer object. The bracket positions and archwire configuration for the corrected teeth are then calculated. Finally, the computer calculates the bending of the archwire configuration that would be necessary when the brackets are so positioned on the teeth, and the teeth are back at their current, uncorrected position. This bent configuration of the archwire is then considered to be an estimated archwire configuration.

The orthodontist may view the ideal bent configuration on a screen and make further adjustments to the digital model of the bent archwire in accordance with his/her further knowledge of the patient and other considerations that may be too complex for the computer to consider. Accordingly, the formation of the computer-generated estimated ideal bent configuration of the archwire may be done with, or without, the assistance of a user. Alternatively, the computer may provide no analysis at all as to the ideal bent configuration of the archwire other than responding to specific instructions from a user regarding the bent configuration.

The method 500 also includes an act of generating a holographic image of the bent orthodontic bracket archwire based on the digital representation (act 514). This may be accomplished using, for example, conventional holographic image projection devices. In FIG. 3, for example, the holographic image is generated by holographic module 305.

This creation of a holographic archwire image allows a user to view the holographic image (act 521) and then manually bend a physical orthodontic bracket archwire using the holographic image as a guide (act 522). For example, the user may manually bend an orthodontic bracket archwire to have the same bending configuration as the holographic image of the bent orthodontic bracket archwire. Accordingly, the user may obtain a high degree of precision in bending the archwire since the holographic image of the archwire reflects computerized assistance and/ or the careful thought and reflection of a user regarding the ideal form of the archwire. Accordingly, an archwire that is bent with the aid of the holographic image is more likely to result in correct movement of the teeth to a desired corrected position.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes, which come within the meaning and range of equivalency of the claims, are to be embraced within their scope.

What is claimed and desired secured by United States Letters Patent is:

1. In a computer system that includes an input device for scanning into the computer system a digital representation of a patient's teeth, a method for facilitating precision bending of an orthodontic archwire that is to be connected to orthodontic brackets so that when affixed to the patient's teeth the brackets and the archwire will effect a desired orthodontic correction on the patient's teeth, the method comprising the following:

a step for scanning into the computer system a digital representation of the patient's teeth;

a step for obtaining a digital representation of an orthodontic archwire having a proposed bending configuration that is designed to effect a desired orthodontic correction when connected to the orthodontic brackets and placed on the patient's teeth; and an act of generating a three dimensional guide in the form of a holographic image of the proposed bending configuration for the archwire, wherein the three dimensional guide is then usable by a practitioner as a template from which to create an actual bending of an archwire in conformity with the generated three dimensional guide displayed as the holographic image.

2. The computer program product for use in a computer system that includes an input device for scanning into the computer system a digital representation of a patient's teeth, the computer program product comprising one or more computer-readable media having stored thereon computer-executable instructions that, when executed, cause the computer system to implement a method for facilitating a precision bending of an orthodontic archwire that is to be connected to orthodontic brackets so that when affixed to the patient's teeth the brackets and the archwire will effect a desired orthodontic correction on the patient's teeth and wherein the method comprises:

a step for scanning into the computer system a digital representation of the patient's teeth;

a step for obtaining a digital representation of an orthodontic archwire having a proposed bending configuration that is designed to effect a desired orthodontic correction when connected to the orthodontic brackets and place on the patient's teeth; and an act of generating a three dimensional guide in the form of a holographic image of the proposed bending configuration for the bracket-archwire, wherein the three dimensional guide is then usable by a practitioner as a template from which to create an actual bending of the archwire in conformity with the generated three dimensional guide displayed as the holographic image.

3. The method as defined in claims 1 or 2, wherein the step for obtaining a digital representation of an orthodontic archwire comprises the following:

an act of receiving user input regarding how to bend an orthodontic archwire; and an act of generating the digital representation of the orthodontic archwire based at least in part on the user input.

4. The method as defined in claim 3, wherein the step for obtaining a digital representation of an orthodontic archwire comprises the following:

an act of a computing system automatically identifying an estimated ideal bent configuration of the orthodontic archwire; and an act of generating the digital representation of the orthodontic archwire based at least in part on the estimated ideal bent configuration.

5. The method as defined in claim 3, wherein the act of receiving user input regarding how to bend an orthodontic archwire comprises the following:

an act of receiving user input regarding one or more modifications required to achieve an estimated ideal bent configuration of the orthodontic archwire.

6. The method as defined in claim 5, wherein the act of generating the digital representation of the archwire based at least in part on the estimated ideal bent configuration comprises the following:

an act of using the estimated ideal bent configuration with the one or more modifications as the generated digital representation.

7. The method as defined in claims 1 or 2, wherein the step for obtaining a digital representation of an orthodontic archwire comprises the following:

an act of a computing system automatically identifying an estimated ideal bent configuration of the orthodontic archwire; and an act of generating the digital representation of the orthodontic archwire based at least in part on the estimated ideal bent configuration.

8. In a computer system that includes an input device for scanning into the computer system a digital representation of a patient's teeth, a method for facilitating precision bending of an orthodontic archwire that is to be connected to orthodontic brackets so that when affixed to the patient's teeth the brackets and the archwire will effect a desired orthodontic correction on the patient's teeth, the method comprising the following:

an act of scanning the patient's teeth with the input device;

an act of generating a digital representation of the patient's teeth;

an act of the computer system automatically identifying a proposed bending configuration for an orthodontic archwire that is designed to effect a desired orthodontic correction when connected to the orthodontic brackets and placed on the patient's teeth;

an act of generating a digital representation of the orthodontic archwire based at least in part on the proposed configuration; and an act of generating a three dimensional guide in the form of a holographic image of the proposed bending configuration for the archwire, wherein the three dimensional guide is then usable by a practitioner as a template from which to create an actual bending of an archwire in conformity with the generated three dimensional guide displayed as the holographic image.

9. A computer program product for use in a computer system that includes an input device for scanning into the computer system a digital representation of a patient's teeth, the computer program product comprising one or more computer-readable media having stored thereon computer-executable instructions that, when executed, cause the computer system to implement a method for facilitating precision bending of an orthodontic archwire that is to be connected to orthodontic brackets so that when affixed to the patient's teeth the brackets and the archwire will effect a desired orthodontic correction of the patient's teeth and wherein the method comprises:

an act of scanning the patient's teeth with the input device;

an act of generating a digital representation of the patient's teeth;

an act of identifying a proposed bending configuration for an orthodontic archwire that is designed to effect a desired orthodontic correction when connected to the orthodontic brackets and placed on the patient's teeth;

an act of generating a digital representation of the orthodontic archwire based at least in part on the proposed bending configuration; and an act of generating a three dimensional guide in the form of a holographic image of the proposed bending configuration for the archwire, wherein the three dimensional guide is then usable by a practitioner as a template from which to create an actual bending of an archwire in conformity with the generated three dimensional guide displayed as the holographic image.

10. The method as defined in claim 8 or 9, further comprising the following:

an act of receiving user input regarding how to bend an orthodontic archwire, wherein the act of generating a digital representation of the orthodontic archwire further comprises the following:

an act of generating the digital representation of the orthodontic archwire based at least in part on the user input.

11. The method as defined in claim 10, wherein the act of receiving user input regarding how to bend an orthodontic bracket archwire comprises the following:

an act of receiving user input regarding one or more modifications to the proposed bending configuration of the orthodontic archwire.

12. The method as defined in claim 11, wherein the act of generating the digital representation of the archwire based at least in part on the proposal bending configuration comprises the following:

an act of using the proposed bending configuration with the one or more modifications as the generated digital representation.

* * * * *